US00PP36383P2

(12) United States Plant Patent
Fleck et al.

(10) Patent No.: US PP36,383 P2
(45) Date of Patent: Jan. 14, 2025

(54) ALMOND TREE NAMED 'BRD38.148'

(50) Latin Name: *Prunus dulcis*
Varietal Denomination: BRD38.148

(71) Applicant: Sierra Gold Nurseries, Inc., Yuba City, CA (US)

(72) Inventors: Charles Edward Fleck, Yuba City, CA (US); Reid Robinson, Yuba City, CA (US)

(73) Assignee: Sierra Gold Nurseries, Inc., Yuba City, CA (US)

( * ) Notice: Subject to any disclaimer, the term of this patent is extended or adjusted under 35 U.S.C. 154(b) by 0 days.

(21) Appl. No.: 18/623,980

(22) Filed: Apr. 1, 2024

(51) Int. Cl.
*A01H 5/10* (2018.01)
*A01H 6/74* (2018.01)

(52) U.S. Cl.
USPC ..... Plt./155

(58) Field of Classification Search
USPC ..... Plt./155
CPC ... A01H 5/10; A01H 5/00; A01H 5/08; A01H 6/7427; A01H 6/74
See application file for complete search history.

(56) References Cited

U.S. PATENT DOCUMENTS

PP29,675 P3 * 9/2018 Wirthensohn ..... A01H 6/7427 Plt./155
PP29,676 P3 * 9/2018 Wirthensohn ..... A01H 6/7427 Plt./155

* cited by examiner

*Primary Examiner* — June Hwu
(74) *Attorney, Agent, or Firm* — Michelle Bos Legal LLC

(57) ABSTRACT

A new and distinct almond tree named 'BRD38.148' distinguished by its upright-spreading growth habit, graft-compatibility with standard and plum-derived almond rootstocks, and early harvest maturity. Fruit of 'BRD38.148' has a well-sealed hull and a large, light-colored kernel.

7 Drawing Sheets

Latin name: *Prunus dulcis.*
Variety denomination: 'BRD38.148'.

BACKGROUND OF THE VARIETY

'BRD38.148' is a new and distinct almond tree. Originally selected from among seedlings resulting from the pollination in 2018 of 'Nonpareil' almond trees (not patented) using mass bulk pollen obtained from self-fertile experimental almond trees, 'BRD38.148' was first propagated by bud-grafting onto commercial almond rootstocks in 2019. Crossing, selection and asexual propagation were carried out at Yuba City, California. The variety has since been asexually reproduced through successive generations and has been observed to remain true to type.

BRIEF DESCRIPTION OF THE VARIETY

The self-fertile 'BRD38.148' almond tree was selected for its desirable horticultural traits, including its upright-spreading growth habit, graft-compatibility with standard and plum-derived almond rootstocks, and early harvest maturity. Fruit of 'BRD38.148' has a well-sealed paper-shell, a widely-opening easily-removed hull and a large, light-colored kernel.

The 'BRD38.148' almond tree is distinguished from female parent 'Nonpareil' as set forth in Table 1 below.

TABLE 1

Comparison of 'BRD38.148' to 'Nonpareil'

| Characteristic | 'BRD38.148' | 'Nonpareil' |
|---|---|---|
| Self-pollinating | Present | Absent |
| Harvest maturity | 7 to 10 days before 'Nonpareil' | Early August |
| Bloom time | 4 to 5 days before 'Nonpareil' | Mid-February |
| Percentage of double kernels | Less than 1% | 3% to 5% or higher |
| Kernel color | Very uniform color; light, greyed-orange 165B | Variable color; greyed-orange 165B with prominent dark veins greyed-orange 165B |
| Kernel size | Average 1.38 g | Average 1.18 g |

'BRD38.148' is distinguishable from known almond varieties 'Carina' (U.S. Plant Pat. No. 29,676) and 'Alm-21' (syn. 'Independence'; U.S. Plant Pat. No. 20,295) by its earlier harvest date. 'BRD38.148' ripens for harvest about 8 days earlier than 'Alm-1' almond and about 2 days earlier than 'Carina' almond.

BRIEF DESCRIPTION OF THE PHOTOGRAPHS

FIG. 1 shows a six-year-old tree of the claimed variety;
FIG. 2 shows a dormant branch and buds of the claimed variety;
FIG. 3 shows flowers and sepals of the claimed variety;
FIG. 4 shows the flowers of the claimed variety;
FIG. 5 shows a branch and leaves of the claimed variety;
FIG. 6 shows the upper and lower surfaces of leaves of the claimed variety;

FIG. 10 shows the unique Genotype of BRD38.148, as described by seven SNP genetic markers.

DETAILED BOTANICAL DESCRIPTION OF THE VARIETY

Figure 1:
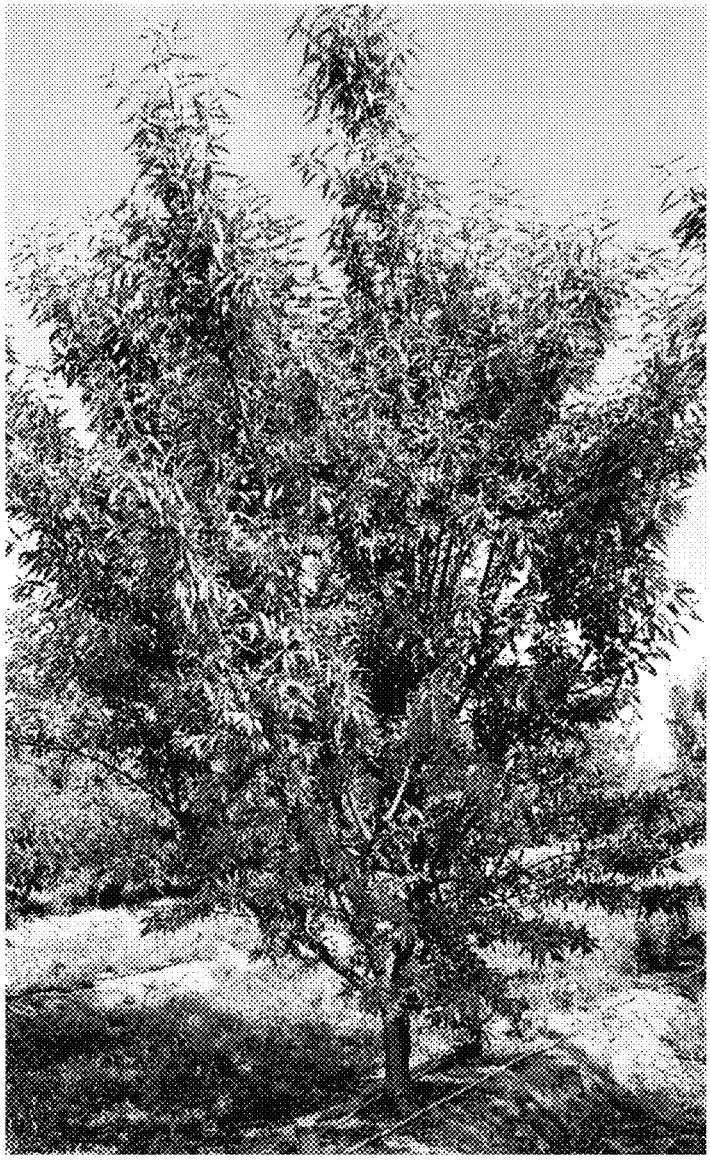
Figure 2:
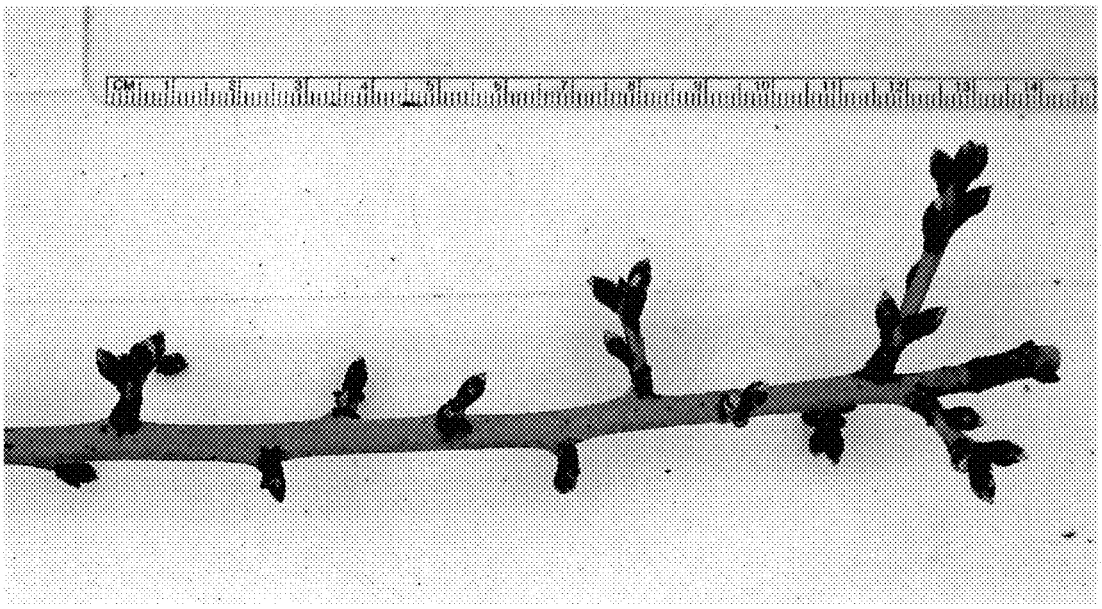
Figure 3:
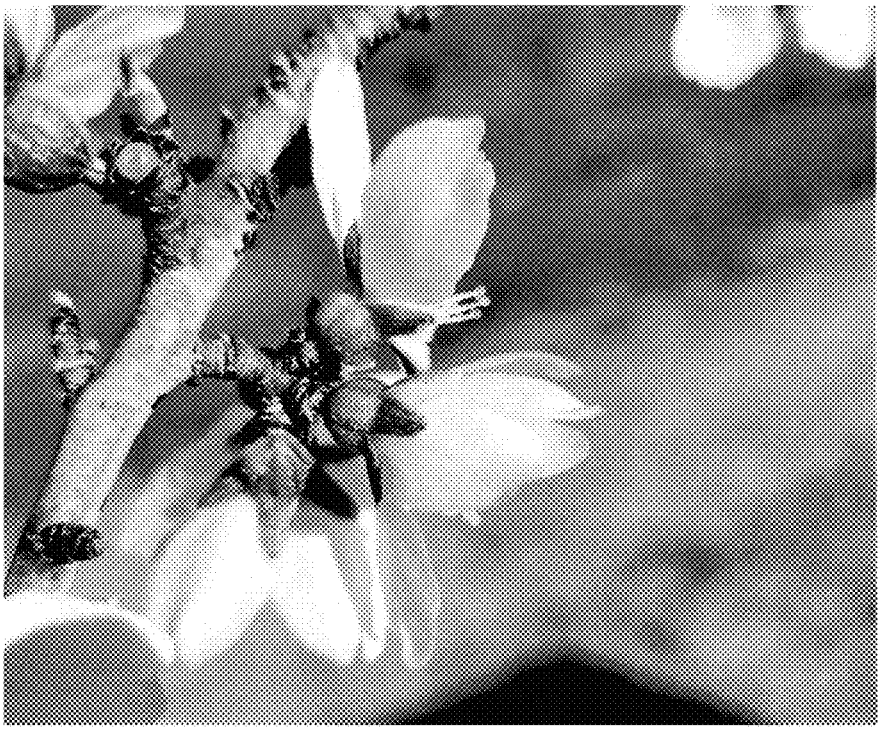
Figure 4:
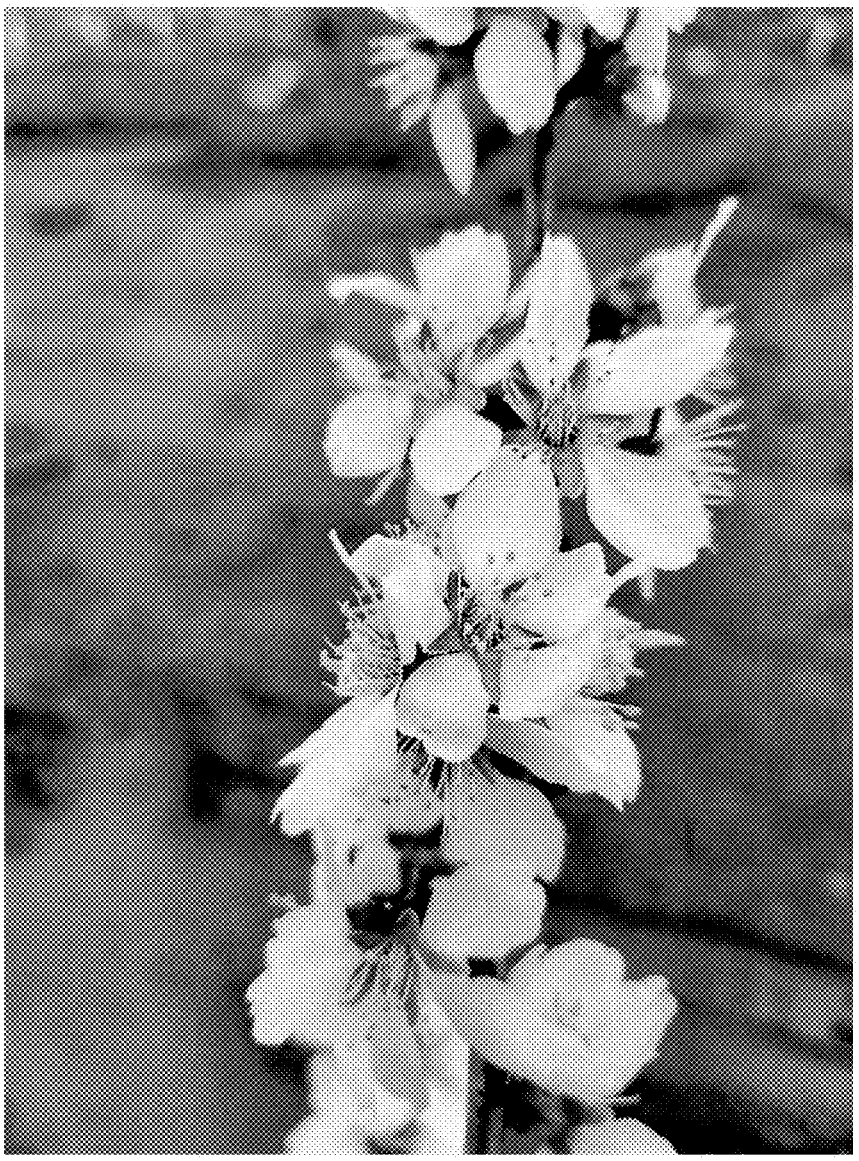
Figure 5:
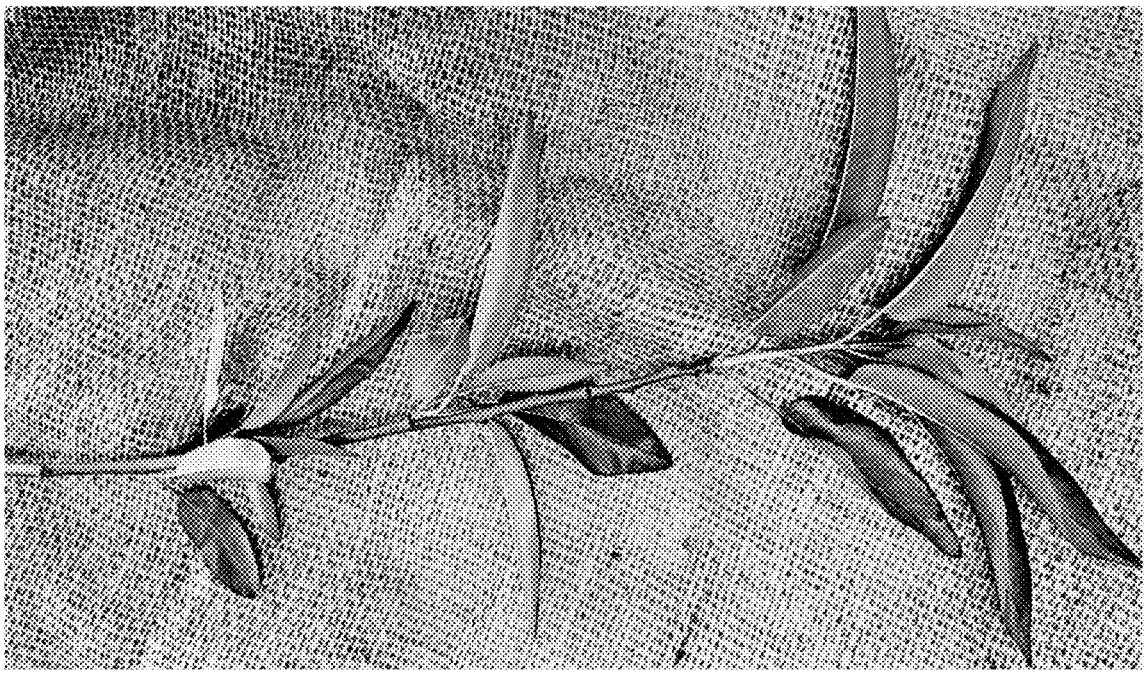
Figure 6:
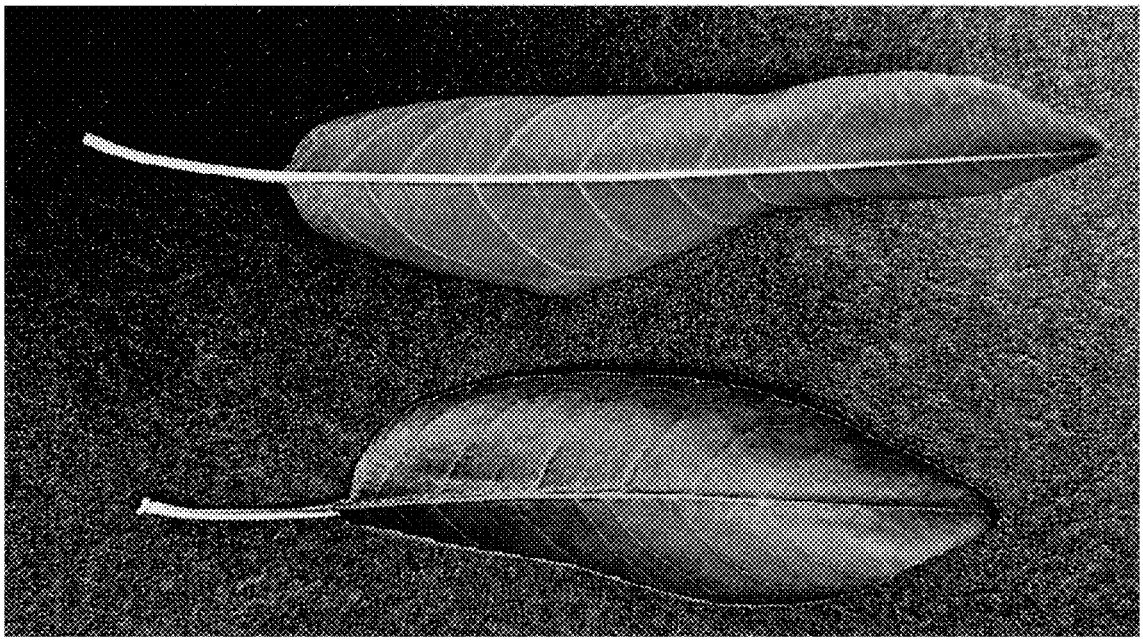
Figure 7:
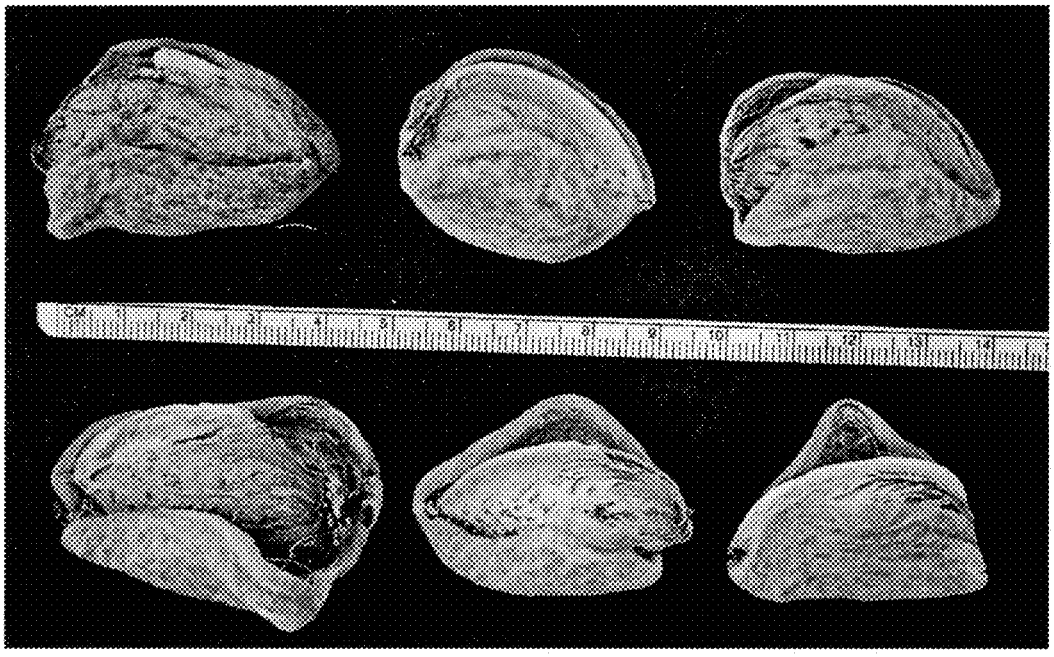
FIG. 7 shows the hull of the fruit of the claimed variety.
Figure 8:
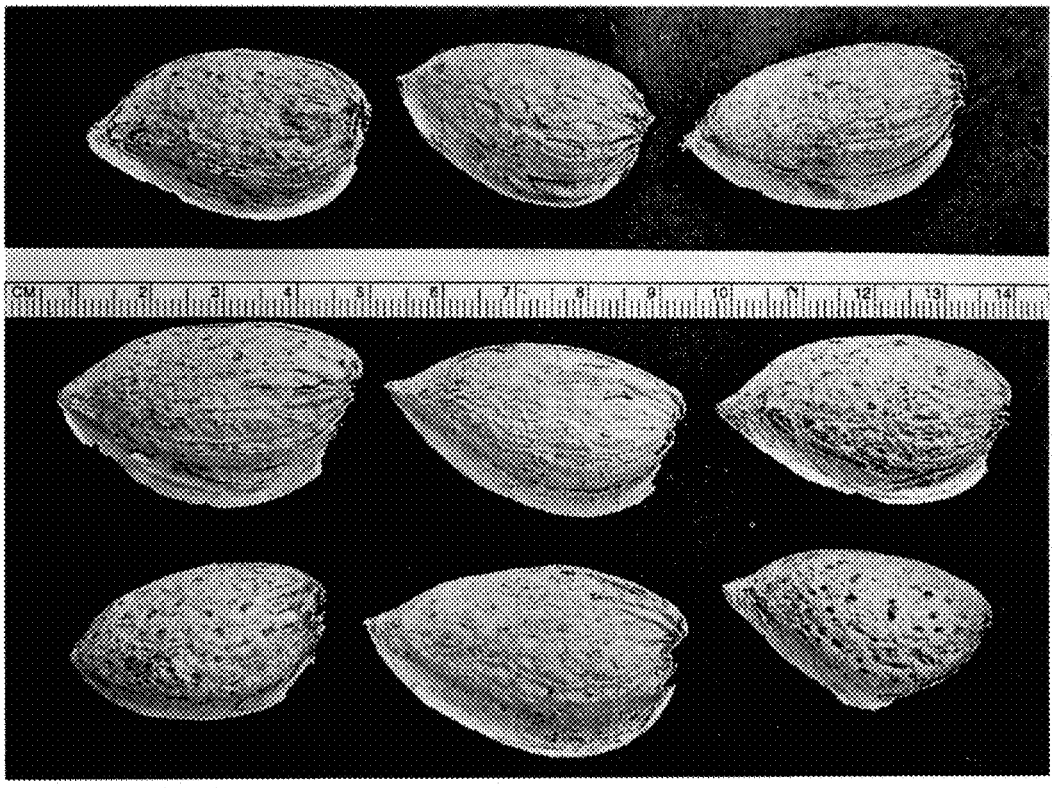
FIG. 8 shows the shell of the of the fruit of the claimed variety.
Figure 9:
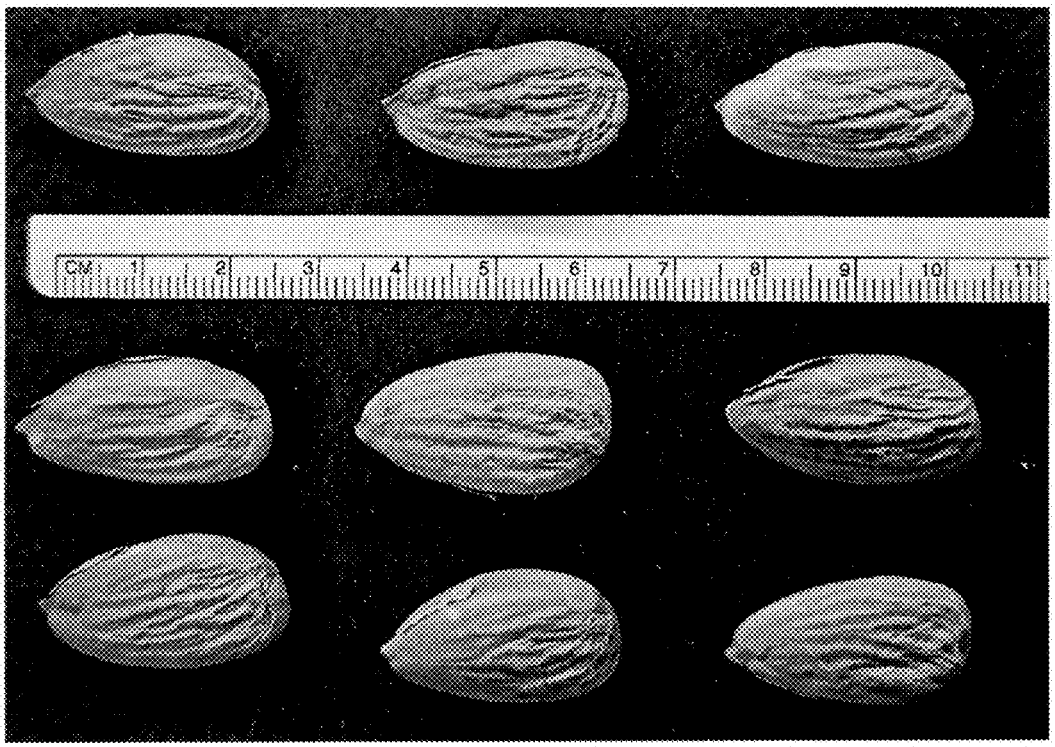
FIG. 9 shows the kernel of the fruit of the claimed variety.

The following-detailed botanical description is based on observations made at Yuba City, California during the 2023 and 2024 growing seasons (unless otherwise noted), of a 6- and 7-year-old trees grown on Krymsk® 86 rootstock ('AP 1' variety, U.S. Plant Pat. No. 16,272). All colors are described according to The R.H.S. Colour Chart (Royal Horticultural Society, London, $6^{th}$ edition 2015). It should be understood that the characteristics described will vary somewhat depending upon cultural practices and climatic conditions and will vary with location and season. Quantified botanical measurements are expressed as an average of measurements taken from a number of measurements on a single mature tree of the new variety. The measurements of any individual plant or any group of plants of the new variety may vary from the stated average.

Tree:

*Vigor*.—Moderately vigorous for cultivated almond.
*Habit*.—Upright-spreading with rounded crown.
*Density*.—Moderate.
*Height*.—5.4 m.
*Spread*.—3.8 m.
*Trunk diameter at* 30 *cm above the graft*.—18.5 cm.
*Bark texture*.—Rough.
*Bark color*.—Greyed-orange 175A.
*Lenticel size*.—1 mm to 2 mm high; 7 mm to 10 mm wide.
*Lenticel color*.—Grey 201C.
*Fertility*.—Self-fertile.

Branch (fruiting branches located at around 1 m above the graft union):

*Length*.—55 cm to 250 cm.
*Diameter*.—15 mm to 22 mm.
*Crotch angle*.—Varies from about 60° to 90°.
*Bark color*.—Greyed-orange 165A.
*Bark texture*.—Smooth.
*Lenticel size*.—1 mm to 1.5 mm high; 3 mm to 4 mm wide.
*Lenticel color*.—Greyed-purple N187D.
*Lenticel density per* $cm^2$.—Varies from 3 to 12.

One-year-old shoot:

*Length*.—12 cm to 34 cm.
*Diameter*.—11 mm to 14 mm.
*Pubescence*.—None.
*Color*.—Greyed-orange 166A on sun side; yellow-green 144B on shaded side.
*Internode length*.—10 mm to 15 mm.
*Distribution of flower buds*.—Balanced equally between shoots and spurs.
*Lenticels*.—Not evident on shoot.

Current year shoots:

*Feathering of secondary shoots*.—Weak to medium.

Flower buds:

*Bud shape*.—Conical.
*Apex shape*.—Acute.
*Length*.—5 mm to 6 mm.
*Diameter*.—3 mm to 4 mm.
*Bud color*.—Greyed-purple 183A.
*Petal tip color just before opening*.—Red-purple N74D.
*Date of bud burst*.—15 Jan. (2024).

Flowers:

*Diameter of fully open flower*.—35 mm to 40 mm.
*Depth of fully open flower*.—6 mm to 7 mm.
*Relative position of petal margin*.—Not touching.
*Pedicel length*.—1 mm.
*Pedicel diameter*.—2 mm.
*Pedicel color*.—Yellow-green N144C.
*Number of flowers per cluster*.—4 to 5.
*Date of first bloom*.—9 Feb. (2024).
*Date of full bloom*.—17 Feb. (2024).
*Pollination requirement*.—Self-pollinating.

Petals:

*Number per flower*.—5.
*Length*.—18 mm to 20 mm.
*Width*.—14 mm.
*Petal shape*.—Obovate.
*Apex shape*.—Emarginate.
*Base shape*.—Attenuate.
*Margin*.—Entire.
*Color of upper surface*.—White 155D and red-purple NN74C near base.
*Color of lower surface*.—White 155B and red-purple N57C near base.

Pistil:

*Length*.—15 mm.
*Color*.—Yellow 1D.

Stigma:

*Diameter*.—1 mm.
*Color*.—Yellow-green 151D.
*Position relative to anthers*.—Varies; usually at the same level.

Style:

*Length*.—7 mm.
*Color*.—Yellow 1D.

Ovary:

*Length*.—2 mm.
*Color*.—Yellow 1C.

Stamens:

*Quantity*.—31 to 35.
*Anther length*.—1 mm.
*Anther color*.—Yellow 7A.
*Filament size*.—Length 7 mm to 8 mm; diameter <1 mm.
*Filament color*.—White NN155D; anthocyanin coloration absent.
*Pollen*.—Present, abundant.
*Pollen color*.—Yellow-green 153D.

Sepals:

*Quantity*.—Five.
*Color*.—Greyed-orange 175A and yellow-green 144B.
*Sepal shape*.—Deltoid.
*Apex shape*.—Apiculate.
*Base shape*.—Fused, cup-like, covering the hypanthium.
*Length*.—6 mm to 7 mm.
*Width*.—4 mm to 5 mm.
*Margin*.—Entire.

Leaves:

*Timing of leaf bud burst*.—Notably later than the beginning of flowering.

*Length*.—7.2 cm to 12.2 cm.

*Width*.—2.2 cm to 2.9 cm.

*Blade margin*.—Serrulate.

*Leaf shape*.—Lanceolate.

*Apex shape*.—Acute.

*Base shape*.—Elliptic.

*Texture of upper surface*.—Smooth; venation not prominent.

*Attitude in relation to shoot*.—Outward.

*Color of upper surface*.—Green 137A.

*Color of lower surface*.—Yellow-green 146B.

*Glands*.—0, 1 or 2 per leaf, usually 1; inconspicuous when present, 0.3 mm to 0.5 mm long, semi-hemispherical to bulbously hemispherical; yellow green N144A.

Petiole:

*Length*.—14 mm to 24 mm.

*Diameter*.—1.5 mm to 2.0 mm.

*Color*.—Yellow-green 144A.

Fruit:

*Quantity per cluster*.—1 to 5, rarely 6.

*Hull diameter*.—19 mm to 24 mm.

*Hull length*.—38 mm to 44 mm.

*Hull texture*.—Smooth, uniformly pubescent.

*Hull color*.—Greyed-yellow 161B.

*Splitting*.—Varies, 20% to 60%.

*Depth of suture*.—Shallow suture, <2 mm.

*Green fruit*.—Ovate with acute apex; moderate pubescence.

Stalk:

*Length*.—0.1 mm to 5.9 mm.

*Diameter*.—2.8 mm to 3.2 mm.

*Color*.—Grey-brown N199A.

Shell:

*Length*.—36 mm to 44 mm.

*Diameter*.—17 mm to 23 mm.

*Shell shape*.—Ovate.

*Apex shape*.—Usually acute; occasionally slightly obtuse.

*Thickness*.—0.9 mm to 1.2 mm.

*Color*.—Greyed-orange 164A to greyed-orange 164C.

*Pit size*.—Mostly <1 mm.

*Pit density*.—0 to 11 per $cm^2$.

*Wing prominence*.—Moderate to highly prominent suture wing.

*Resistance to cracking*.—Weak to medium.

Kernel:

*Length*.—24 mm to 28 mm.

*Diameter*.—11 mm to 16 mm.

*Thickness*.—7 mm to 9 mm.

*Weight*.—1.1 g to 1.8 g; average 1.4 g.

*Overall shape*.—Ovate to elliptical.

*Apex shape*.—Obtusely apiculate.

*Color*.—Very light, greyed-orange 165B.

*Surface texture*.—Relatively smooth.

*Pubescence*.—Very slight.

*Pellicle thickness*.—Varies, 0.20 mm to 0.50 mm.

*Pellicle tenacity*.—High, similar to most commercial almond varieties.

*Frequency of doubles*.—Significantly less than 0.5%.

*Taste*.—Mildly sweet.

Harvest: Mechanical commercial harvest with tree-shaking machines.

*Harvest timing*.—In the Sacramento Valley of California, last week of July; 7 to 10 days before 'Nonpareil'.

*Productivity per tree per harvest*.—Moderately high to very high.

*Bearing*.—Annual.

Chilling requirement: Approximately 200 to 300 chill hours.

Cold hardiness: Hardy to −10° C.

Disease susceptibility: Moderately susceptible to typical California almond bloom and foliar diseases.

Pest resistance: Highly sealed shell and early harvest reduce Navel Orange Worm and ant susceptibility.

Genotype: The unique genotype of the claimed variety is evidenced in the comparison of seven SNP genetic markers in 'BRD38.148' to the array of current commercial and legacy almond varieties shown in FIG. 10.

Market use: Excellent for in-shell and shelled kernel; blanched, blanched slivered, sliced and roasted kernel products.

The invention claimed is:

1. A new and distinct almond tree named 'BRD38.148' substantially as illustrated and described herein.

* * * * *

| SNP Assay: | WriPdK5 | WriPdK19 | WriPdK25 | WriPdK58 | WriPdK83 | WriPdK89 | WriPdK112 |
|---|---|---|---|---|---|---|---|
| Almond variety | | | | | | | |
| **BRD38.148** | T/C | G | A | T | T/C | T | C |
| Aldrich | T/C | G | A/C | T | T | T | T/C |
| Booth | T/C | G/A | A/C | T | T/C | T | C |
| Butte | C | G | C | T | T | T | C |
| Carmel O.S. | C | G | C | T | T | T | C |
| CRT | T/C | G/A | A/C | T | T/C | T | C |
| Fritz | T/C | G | A/C | T | T | T | C |
| Independence | C | G/A | A/C | T | T | T | T/C |
| Kester | C | G/A | A | T/C | T/C | T | C |
| Lauranne | C | G | A | T/C | T | G/T | T/C |
| Marcona | C | G/A | A | T | T | T | C |
| Monterey | T/C | G/A | C | T | T | T | T/C |
| Ne Plus | C | G/A | A/C | T | T/C | T | C |
| Nonpareil | T/C | G/A | A/C | T | T/C | T | C |
| Padre | C | G/A | A | T/C | T | T | C |
| Peerless | T/C | G/A | C | T | T/C | T | C |
| Price | C | G/A | A/C | T | T/C | T | C |
| Shasta | C | G/A | A/C | T/C | T | G/T | T/C |
| Sonora | C | G/A | C | T | T | T | C |
| Sweetheart | C | A | A/C | T | T | T | C |
| Texas Mission | T/C | G | A/C | T | T | T | T/C |
| Winters | C | G/A | C | C | T | T | C |
| Wood Colony | C | G | A | T | T | T | T/C |
| Yorizane | C | A | A/C | T | T | G/T | T/C |

| | | | | | | | |
|---|---|---|---|---|---|---|---|
| Allele 1 | T | G | A | T | T | G | T |
| Allele 1/2 | T/C | G/A | A/C | T/C | T/C | G/T | T/C |
| Allele 2 | C | A | C | C | C | T | C |

*FIG. 10*